(12) United States Patent
Maywald et al.

(10) Patent No.: US 11,591,293 B2
(45) Date of Patent: Feb. 28, 2023

(54) MANUFACTURING METHOD FOR AN AROMATIC ISOCYANATE COMPOUND

(71) Applicant: BASF SE, Ludwigshafen (DE)

(72) Inventors: Volker Maywald, Ludwigshafen (DE); Roland Goetz, Neulussheim (DE); Daniel Saelinger, Ludwigshafen (DE); Birgit Gockel, Ludwigshafen (DE); Manfred Ehresmann, Ludwigshafen (DE); Markus Jegelka, Ludwigshafen (DE); Joaquim Henrique Teles, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 17/296,683

(22) PCT Filed: Dec. 11, 2019

(86) PCT No.: PCT/EP2019/084545
§ 371 (c)(1),
(2) Date: May 25, 2021

(87) PCT Pub. No.: WO2020/126716
PCT Pub. Date: Jun. 25, 2020

(65) Prior Publication Data
US 2022/0024864 A1 Jan. 27, 2022

(30) Foreign Application Priority Data

Dec. 20, 2018 (EP) ..................................... 18214612
May 10, 2019 (EP) ..................................... 19173679

(51) Int. Cl.
*C07C 263/10* (2006.01)
(52) U.S. Cl.
CPC ................................. *C07C 263/10* (2013.01)
(58) Field of Classification Search
CPC ... C07C 263/10; C07C 265/12; C09K 3/1445; H01B 1/02; H01F 1/032; H01F 1/04; H01F 1/20; H01F 1/33; H01F 41/02
See application file for complete search history.

(56) References Cited

U.S. PATENT DOCUMENTS

| | | | | | |
|---|---|---|---|---|---|
| 4,879,408 | A | * | 11/1989 | Knofel | C07C 265/10 560/330 |
| 2011/0190535 | A1 | * | 8/2011 | Carr | C08G 12/08 564/315 |

FOREIGN PATENT DOCUMENTS

| EP | 2990404 A1 * | 3/2016 | ........... A01N 43/713 |
|---|---|---|---|
| EP | 3235807 A1 | 10/2017 | |
| EP | 3392238 A1 | 10/2018 | |
| WO | WO-01/17951 A1 | 3/2001 | |
| WO | WO-0200628 A2 * | 1/2002 | ........... C07D 239/30 |
| WO | WO-2013/162072 A1 | 10/2013 | |

OTHER PUBLICATIONS

European Search Report for EP Patent Application No. 19173679.2, dated Nov. 21, 2019, 3 pages.
Petursson, "Product class: 8 Ethers as Protecting Groups", Science of Synthesis, Ed. C. J. Forsyth, vol. 37, 2008, p. 858.
International Application No. PCT/EP2019/084545, International Search Report and Written Opinion, dated Feb. 20, 2020.

* cited by examiner

*Primary Examiner* — Yevgeny Valenrod
*Assistant Examiner* — Blaine G Doletski
(74) *Attorney, Agent, or Firm* — Marshall, Gerstein & Borun LLP

(57) ABSTRACT

A method for manufacturing an isocyanate compound represented by formula (2) (2) wherein R1 represents a methyl group, an ethyl group, a cyclopropyl group, a chlorine atom, a bromine atom, or a methoxy group; and R2 represents an alkyl group having 1 to 6 carbon atoms, comprising reacting an aniline compound represented by formula (1) (1) wherein R1 and R2 are defined as above with a phosgene compound at a temperature of from 40° C. to the boiling point of the inert solvent in at least one kind of inert solvent.

15 Claims, No Drawings

MANUFACTURING METHOD FOR AN AROMATIC ISOCYANATE COMPOUND

CROSS-REFERENCE TO RELATED APPLICATIONS

This is the U.S. national phase of International Application No. PCT/EP2019/084545, filed Dec. 11, 2019, which claims the benefit of European Patent Application No. 18214612.6, filed on Dec. 20, 2018, and European Patent Application No. 19173679.2, filed May 10, 2019.

The present invention relates to a manufacturing method for aromatic isocyanate compounds, particularly 1-isocyanato-2-(alkoxymethyl)-3-alkyl-benzenes, which are important intermediates used in the synthesis of crop protection agents, see for example WO 2013/162072.

EP 3235807 A1 discloses a process for producing 1-isocyanato-2-(alkoxymethyl)-3-alkylbenzenes which comprises reacting 2-alkoxymethyl-3-alkyl-anilines with a phosgene compound, for example triphosgene, in the presence of a tertiary amine at 10° C. to 14° C. in at least one kind of solvent selected from the group consisting of chlorobenzene and orthodichlorobenzene.

EP 3392238 A1 discloses a process for producing 1-isocyanato-2-(alkoxymethyl)-3-alkylbenzenes which comprises reacting 2-alkoxymethyl-3-alkyl-anilines with phosgene in the presence of a tertiary amine at 9° C. to 16° C. in one or more solvents selected from the group consisting of toluene and xylene.

WO 01/17951 discloses a process for producing aliphatic, cycloaliphatic, araliphatic and aromatic mono- and oligoisocyanates via phosgenation of primary amines using catalytic amounts of a monoisocyanate at temperatures from 50° C. to 120° C. in an inert solvent.

However, the processes disclosed in EP 3235807 A1 and EP 3392238 A1 have two main disadvantages. The first disadvantage is that these processes are only operable in a very narrow and low temperature range, the yield of the 1-isocyanato-2-(alkoxymethyl)-3-alkyl-benzenes decreases significantly outside this temperature range. The second disadvantage is that these processes require the use of large amounts of tertiary amines, such as triethylamine. These tertiary amines have to be removed during the workup of the reaction mixture, for example as ammonium hydrochlorides by filtration. On industrial scale, the filtration of such ammonium hydrochlorides often causes problems due to the small particle size of the ammonium hydrochloride crystals and therefore only filtration apparatuses fulfilling specific requirements can be used. Furthermore, parts of the ammonium chlorides can remain in the product and thus reduce the quality and the stability of the 1-isocyanato-2-(alkoxymethyl)-3-alkyl-benzenes.

Furthermore, ammonium hydrochlorides have the unfavourable property to form deposits in exhaust gas systems of production equipment, which can be a safety risk and causes increased cleaning efforts. It is therefore desirable to minimize the amount of alkylamines used in the phosgenation process.

On the other hand, it is a known problem that alkoxymethyl groups of aromatic compounds (e.g. methyl benzyl ether groups) are acid labile and can be cleaved under phosgenation conditions where stoichiometric amounts of hydrogen chloride are formed at high temperatures. This leads to unwanted side reactions and lower yields (Petursson, S., Science of Synthesis, (2008), 37, 858.) Known processes therefore use high amounts of tertiary amines to trap any hydrochloric acid formed.

It was the objective of the present invention to provide a process for the preparation of 1-isocyanato-2-(alkoxymethyl)-3-alkyl-benzenes in high yields via phosgenation that do not use stoichiometric amounts of tertiary amine bases for trapping the formed hydrogen chloride. It was further an objective to provide a phosgenation process that can be applied under flexible temperature conditions without the necessity to operate under narrowly defined and low temperatures.

These objectives have been achieved by methods for manufacturing an isocyanate compound represented by formula (2)

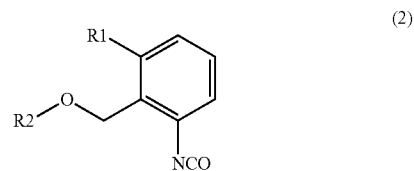

(2)

wherein R1 represents a methyl group, an ethyl group, a cyclopropyl group, a chlorine atom, a bromine atom, or a methoxy group; and R2 represents an alkyl group having 1 to 6 carbon atoms, comprising reacting an aniline compound represented by formula (1)

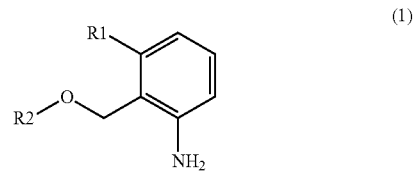

(1)

wherein R1 and R2 are defined as above
with a phosgene compound in at least one kind of inert solvent at a temperature from 40° C. to the boiling point of the inert solvent.

The isocyanate compound represented by above formula (2) wherein R1 represents a methyl group, an ethyl group, a cyclopropyl group, a chlorine atom, a bromine atom, or a methoxy group, and R2 represents an alkyl group having 1 to 6 carbon atoms, is referred to as "isocyanate compound" in the following.

The aniline compound represented by above formula (1) wherein R1 and R2 are defined as above is referred to as "aniline compound" in the following.

The inert solvent to be used in the reaction can be any kind of inert solvent, and is preferably an organic solvent, more preferably an aprotic organic solvent, most preferably an aromatic solvent, particularly preferably a solvent selected from the group consisting of benzene, alkylated benzenes, and halogenated benzenes, particularly more preferably toluene, xylene, chlorobenzene, or dichlorobenzene, for example toluene. In case of xylene, o-xylene, m-xylene, p-xylene or a mixture thereof can be used. In case of dichlorobenzene, 1,2-dichlorobenzene, 1,3-dichlorobenzene, 1,4-dichlorobenzene, or a mixture thereof can be used.

The term "inert" in "inert solvent" means that the solvent is not able to undergo chemical reactions with the reactants under the reaction conditions.

The phosgene compound to be used in the reaction is phosgene, diphosgene (trichloromethyl chloroformate) or triphosgene (bis(trichloromethyl) carbonate), and is preferably phosgene.

The reaction temperature ranges from 40° C. to the boiling point of the inert solvent. The reaction temperature is not less than 40° C., preferably not less than 45° C., more preferably not less than 50° C., particularly preferably not less than 55° C., particularly more preferably not less than 60° C., particularly most preferably not less than 65° C., particularly not less than 70° C., for example not less than 75° C. The reaction temperature is not more than the boiling point of the inert solvent, preferably not more than 110° C., more preferably not more than 105° C., particularly preferably not more than 100° C., particularly more preferably not more than 95° C., for example not more than 90° C.

In a preferred embodiment of the present invention, the reaction temperature ranges from 50° C. to 100° C., more preferably from 60° C. to 95° C., most preferably from 75 to 90° C.

In another preferred embodiment of the present invention, the reaction temperature ranges from 80° C. to 95° C., more preferably from 83° C. to 90° C., most preferably from 85° C. to 88° C.

In another preferred embodiment of the present invention, the reaction temperature ranges from 70° C. to 85° C., more preferably from 73° C. to 83° C., most preferably from 75° C. to 80° C.

In another preferred embodiment of the present invention,
a) the aniline compound, and
b) the phosgene compound,
are added to a solution comprising at least one kind of inert solvent.

The solution comprising at least one kind of inert solvent is referred to as "solution (S1)" in the following.

In another preferred embodiment of the present invention, the addition of the aniline compound or of the phosgene compound occurs below the liquid surface of solution (S1).

In another preferred embodiment of the present invention, the addition of the aniline compound occurs below the liquid surface of solution (S1).

In another preferred embodiment of the present invention, the addition of the phosgene compound occurs below the liquid surface of solution (S1). More preferably, the addition of phosgene occurs below the liquid surface of solution (S1).

In another preferred embodiment of the present invention, the addition of the aniline compound and of the phosgene compound occurs below the liquid surface of solution (S1). More preferably, the addition of the aniline compound and of phosgene occurs below the liquid surface of solution (S1).

In another preferred embodiment of the present invention, the addition of the aniline compound and/or of the phosgene compound occurs below the liquid surface of solution (S1). In another preferred embodiment of the present invention, the addition of the aniline compound and/or of the phosgene compound occurs below the liquid surface of solution (S1) and is conducted via dip pipes or mixing nozzles. More preferably, the addition of the aniline compound and/or of phosgene occurs below the liquid surface of solution (S1). More preferably, the addition of the aniline compound and/or of phosgene occurs below the liquid surface of solution (S1) and is conducted via dip pipes or mixing nozzles.

In another preferred embodiment of the present invention, before the addition of the aniline compound and of the phosgene compound, solution (S1) already comprises the phosgene compound, more preferably phosgene.

In another preferred embodiment of the present invention, R1 in the formula (1) and formula (2) is methyl.

In another preferred embodiment of the present invention, R2 in the formula (1) and formula (2) is methyl, ethyl, propyl, isopropyl, butyl, sec-butyl, tert-butyl, pentyl, or hexyl, more preferably methyl, ethyl, propyl, or isopropyl, most preferably methyl, or ethyl.

In another preferred embodiment of the present invention, R2 in the formula (1) and formula (2) is methyl.

In another preferred embodiment of the present invention, R1 and R2 in the formula (1) and formula (2) is methyl.

In another preferred embodiment of the present invention, the isocyanate to be produced or another isocyanate compound is also used as catalyst for catalyzing the reaction between the aniline compound and phosgene compound.

In another preferred embodiment of the present invention, before the addition of the aniline compound and of the phosgene compound, solution (S1) already comprises an isocyanate compound, for example the planned reaction product, as catalyst, preferably in amounts of 1 to 30 mole-%, more preferably in amounts of 5 to 20 mole-%, most preferably in amounts of 6 to 15 mole-%, particularly in amounts of 7 to 13 mole-%, particularly preferably in amounts of 8 to 12 mole-%, for example in amounts of 9 to 11 mole-% relative to 1 mole of the aniline compound to be added.

It has to be emphasized that high yields of the isocyanate compound can also be achieved without the use of the isocyanate compound as catalyst. Thus, in a preferred embodiment, processes according to the invention are carried out without the addition of any isocyanate compound to the reaction mixture.

In another preferred embodiment of the present invention, processes according to the invention are carried in the absence of any tertiary amines. It has proven especially beneficial to carry the processes according to the invention in the absence of any tertiary amines and at elevated temperatures, for example at 40° C. or above, or at 60° C. or 75° C. or above, or at 85° C. or above.

In another preferred embodiment of the present invention, the molar ratio of the aniline compound to be used in the reaction to the phosgene compound to be used in the reaction is in the range of 1:1 to 1:10, more preferably in the range of 1:1 to 1:5, most preferably in the range of 1:1.5 to 1:4, particularly preferably in the range of 1:2 to 1:3.5, particularly more preferably in the range of 1:2.2 to 1:2.8.

In another preferred embodiment of the present invention, the molar ratio of the aniline compound to be used in the reaction to the phosgene to be used in the reaction is in the range of 1:1 to 1:10, more preferably in the range of 1:1 to 1:5, most preferably in the range of 1:1.5 to 1:4, particularly preferably in the range of 1:2 to 1:3.5, particularly more preferably in the range of 1:2.2 to 1:2.8.

In another preferred embodiment of the present invention, the ratio of the inert solvent—for example toluene—to the aniline compound is in the range of 250 g to 3000 g per mole of aniline compound, more preferably in the range of 500 g to 1500 g per mole of aniline compound, most preferably in the range of 700 g to 1200 g per mole of aniline compound.

In another preferred embodiment of the present invention, the aniline compound to be used in the reaction is present in the form of the pure aniline compound.

In another preferred embodiment of the present invention, the aniline compound to be used in the reaction is present in the form of a 5 wt % to 75 wt % solution of the aniline compound in the inert solvent, more preferably in the form of a 10 wt % to 75 wt % solution of the aniline compound in the inert solvent, even more preferably in the form of a 25 wt % to 50 wt % solution of the aniline compound in the inert solvent, most preferably in the form of a 35 wt % to 45 wt % solution of the aniline compound in the inert solvent.

In another preferred embodiment of the present invention, the aniline compound to be used in the reaction is present in the form of a 5 wt % to 75 wt % solution of the aniline compound in toluene, more preferably in the form of a 10 wt % to 75 wt % solution of the aniline compound in toluene, even more preferably in the form of a 25 wt % to 50 wt % solution of the aniline compound in toluene, most preferably in the form of a 35 wt % to 45 wt % solution of the aniline compound in toluene.

In another preferred embodiment of the present invention, the aniline compound to be used in the reaction is added in the form of a 5 wt % to 75 wt % solution of the aniline compound in the inert solvent, more preferably in the form of a 10 wt % to 75 wt % solution of the aniline compound in the inert solvent, even more preferably in the form of a 25 wt % to 50 wt % solution of the aniline compound in the inert solvent, most preferably in the form of a 35 wt % to 45 wt % solution of the aniline compound in the inert solvent.

In another preferred embodiment of the present invention, the aniline compound to be used in the reaction is added in the form of a 5 wt % to 75 wt % solution of the aniline compound in toluene, more preferably in the form of a 10 wt % to 75 wt % solution of the aniline compound in toluene, even more preferably in the form of a 25 wt % to 50 wt % solution of the aniline compound in toluene, most preferably in the form of a 35 wt % to 45 wt % solution of the aniline compound in toluene.

In another preferred embodiment of the present invention, the time which is needed for adding the aniline compound and the phosgene compound to solution (S1)—i.e. the dosage time—is 1 to 10 hours, more preferably 2 to 5 hours.

In another preferred embodiment of the present invention, the phosgene compound to be used in the reaction—particularly phosgene—can be added to the inert solvent—particularly toluene—as gas, or in condensed form, more preferably as gas.

The reaction is usually done under normal pressure, however, it is also feasible to run the reaction under light vacuum.

In another preferred embodiment of the present invention, dry inert solvent and/or dry reactants, for example dry aniline compound, are used.

In another preferred embodiment of the present invention, the reaction can be conducted as a continuous reaction or as a batch reaction.

In another preferred embodiment of the present invention, the inert solvent is prepared and heated to reaction temperature, subsequently, phosgene is added to saturation, and then the remaining part of the phosgene is added in parallel with the aniline compound.

After the completion of the reaction, the isocyanate compound can be isolated by carrying out a post-treatment procedure. The isocyanate compound may be isolated e.g. as raw product by evaporation of the solvent or may be further purified by procedures such as distillation in case of liquid products or crystallization in case of solid products.

Processes according to the invention offer the following advantages:
They are easy and economical to carry out. They yield the desired product in high yield and purity.
They can be carried out in the absence of any tertiary amines.
They can be carried out at various temperatures, for example above 40° C. and up to the boiling point of the reaction medium.
They can be carried out without the addition of any further isocyanate.

The present invention can be illustrated by the following examples:

EXAMPLES

Example 1:
1-Isocyanato-2-(methoxymethyl)-3-methyl-benzene

Without catalyst (1-Isocyanato-2-(methoxymethyl)-3-methyl-benzene)
Dosage of 2-Methoxy-3-methylaniline and phosgene via dip pipes
Reaction temperature: 85-88° C.
Dosage time: 4 h
Dosage of 2-Methoxy-3-methylaniline as 40 wt % solution in toluene The reaction was carried out in a reactor equipped with a condenser operated at −40° C. 1452.4 g of toluene was precharged at room temperature and the agitator was started. Then the solvent was heated up to 85° C. During the heating-up phase 72.3 g (0.720 mol) of phosgene (98.5 wt % purity) was added. To the boiling mixture of phosgene in toluene were dosed in 4 h at 85-88° C. in parallel 265.1 g (2.640 mol) of phosgene and 528.9 g (1.399 mol) of a 40% solution of 2-Methoxy-3-methylaniline in toluene. Both additions were done below the liquid surface via dip pipes. The formed HCl gas and not condensed phosgene were discharged in a wash column operated with NaOH (10 wt %). After the dosages were completed, the mixture was post-reacted 1 h at 88° C. Then the mixture was cooled down to 50° C. and the excessive phosgene was stripped with nitrogen. For isolation of the product, toluene was distilled off at max. 80° C. under reduced pressure. 255.0 g (1.312 mol) of 1-Isocyanato-2-(methoxymethyl-3-methyl-benzene with a purity of 91.2 wt %, HPLC (after derivatization) was obtained (main impurity: toluene (3.8% wt %, GC)).

Yield: 93.8%
(calculation: 1.312 mol product/1.399 mol starting material×100%)

Example 2:
1-Isocyanato-2-(methoxymethyl)-3-methyl-benzene

With catalyst (1-Isocyanato-2-(methoxymethyl)-3-methyl-benzene)
Dosage of 2-Methoxy-3-methylaniline and phosgene via dip pipes
Reaction temperature: 85-88° C.
Dosage time: 4 h
Dosage of 2-Methoxy-3-methylaniline as 40 wt % solution in toluene The reaction was carried out in a reactor equipped with a condenser operated at −40° C. 1451.8 g of toluene was precharged at room temperature together with 25.2 g (0.140 mol) of the catalyst 1-Isocyanato-2-(methoxymethyl-3-methyl-benzene (98.5 wt % purity) and the agitator was started. Then the solvent was heated up to 85° C. During the heating-up phase 72.0 g (0.717 mol) of phosgene (98.5 wt % purity) were added. To the boiling mixture of phosgene in toluene were dosed in 4 h at 85-88° C. in parallel 266.1 g (2.650 mol) of phosgene and 529.1 g (1.400 mol) of a 40 wt % solution of 2-Methoxy-3-methylaniline in toluene. Both additions were done below the liquid surface via dip pipes. The formed HCl gas and not condensed phosgene were discharged in a wash column operated with NaOH (10 wt %). After the dosages were completed, the mixture was post-reacted 1 h at 88° C. Then the mixture was cooled down to 50° C. and the excessive phosgene was stripped with nitrogen. For isolation of the product, toluene was distilled off at max. 80° C. under reduced pressure. 279.3 g (1.450 mol) of 1-Isocyanato-2-(methoxymethyl-3-methyl-benzene with a purity of 92.0 wt %, HPLC (after derivatization) was obtained (main impurity: toluene (3.1 wt %, GC).

Yield: 93.6%

(calculation: (1.450 mol product−0.140 mol catalyst)/1.400 mol starting material×100%)

Example 3:
1-Isocyanato-2-(methoxymethyl)-3-methyl-benzene

With catalyst (1-Isocyanato-2-(methoxymethyl)-3-methyl-benzene)
Dosage of 2-Methoxy-3-methylaniline and phosgene via dip pipes
Reaction temperature: 65-69° C.
Dosage time: 2 h
Dosage of 2-Methoxy-3-methylaniline as pure substance The reaction was carried out in a reactor equipped with a condenser operated at −40° C. 1498.6 g of toluene was precharged at room temperature together with 26.1 g (0.140 mol) of the catalyst 1-Isocyanato-2-(methoxymethyl-3-methyl-benzene (94.9 wt % purity) and the agitator was started. Then the solvent is heated up to 65° C. During the heating-up phase 170.0 g (1.693 mol) of phosgene (98.5 wt % purity) is added. To the boiling mixture of phosgene in toluene were dosed in 2 h at 65-69° C. in parallel 170.1 g (1.694 mol) of phosgene and 216.0 g (1.410 mol) of 2-Methoxy-3-methylaniline (98.7 wt % purity). Both additions were done below the liquid surface via dip pipes. The formed HCl gas and not condensed phosgene were discharged in a wash column operated with NaOH (10%). After the dosages were completed, the mixture was post-reacted 1 h at 69° C. Then the mixture was cooled down to 50° C. and the excessive phosgene was stripped with nitrogen. For isolation of the product, toluene was distilled off at max. 80° C. under reduced pressure. 279.3 g (1.442 mol) of 1-Isocyanato-2-(methoxymethyl-3-methyl-benzene with a purity of 91.5 wt %, HPLC (after derivatization) was obtained (main impurity: toluene (3.9 wt %, GC)).

Yield: 92.3%

(calculation: (1.442 mol product−0.140 mol catalyst)/1.410 mol starting material×100%)

Example 4:
1-Isocyanato-2-(methoxymethyl)-3-methyl-benzene

With catalyst (1-Isocyanato-2-(methoxymethyl)-3-methyl-benzene)
Dosage of 2-Methoxy-3-methylaniline on the liquid surface
Dosage of phosgene below the liquid surface via dip pipe
Reaction temperature: 65-69° C.
Dosage time: 2 h
Dosage of 2-Methoxy-3-methylaniline as pure substance The reaction was carried out in a reactor equipped with a condenser operated at −40° C. 1499.1 g of toluene was precharged at room temperature together with 26.1 g (0.140 mol) of the catalyst 1-Isocyanato-2-(methoxymethyl-3-methyl-benzene (94.9 wt % purity) and the agitator was started. Then the solvent was heated up to 65° C. During the heating up phase 169.8 g (1.691 mol) of phosgene (98.5 wt % purity) was added. To the boiling mixture of phosgene in toluene were dosed in 2 h at 65-69° C. in parallel 170.5 g (1.698 mol) of phosgene and 214.5 g (1.400 mol) of 2-Methoxy-3-methylaniline (98.7 wt % purity). Only the addition of phosgene was done below the liquid surface via dip pipe, the addition of 2-Methoxy-3-methylaniline was done on the liquid surface. The formed HCl gas and not condensed phosgene were discharged in a wash column operated with NaOH (10 wt %). After the dosages were completed, the mixture was post-reacted 1 h at 69° C. Then the mixture was cooled down to 50° C. and the excessive phosgene was stripped with nitrogen. For isolation of the product, toluene was distilled off at max. 80° C. under reduced pressure. 252.0 g (0.950 mol) of 1-Isocyanato-2-(methoxymethyl-3-methyl-benzene with a purity of 66.8 wt %, HPLC (after derivatization) was obtained. The product was severely contaminated with polymeric by-products.

Yield: 57.9%

(calculation: (0.950 mol product−0.140 mol catalyst)/1.400 mol starting material×100%)

Example 5:
1-Isocyanato-2-(methoxymethyl)-3-methyl-benzene

Without catalyst (1-Isocyanato-2-(methoxymethyl)-3-methyl-benzene)
Dosage of 2-Methoxy-3-methylaniline and phosgene via dip pipes
Reaction temperature: 75-80° C.
Dosage time: 2 h
Dosage of 2-Methoxy-3-methylaniline as 25 wt % solution in toluene The reaction was carried out in a reactor equipped with a condenser operated at −40° C. 1421.0 g of toluene was precharged at room temperature and the agitator was started. Then the solvent was heated up to 75° C. During the heating-up phase 123.4 g (1.229 mol) of phosgene (98.5 wt % purity) was added. To the boiling mixture of phosgene in toluene were dosed in 2 h at 75-80° C. in parallel 297.9 g (2.966 mol) of phosgene and 846.9 g (1.400 mol) of a 25 wt % solution of 2-Methoxy-3-methylaniline in toluene. Both additions were done below the liquid surface via dip pipes. The formed HCl gas and not condensed phosgene were discharged in a wash column operated with NaOH (10 wt %). After the dosages was completed, the mixture was post-reacted 1 h at 80° C. Then the mixture was cooled down to 50° C. and the excessive phosgene was stripped with nitrogen. For isolation of the product, toluene was distilled off at max. 80° C. under reduced pressure. 255.4 g (1.335 mol) of 1-Isocyanato-2-(methoxymethyl-3-methyl-benzene with a purity of 92.6 wt %, HPLC (after derivatization) was obtained (main impurity: toluene (4.1 wt %, GC)).

Yield: 95.4%

(calculation: 1.335 mol product/1.400 mol starting material×100%)

The above examples show that according to the present invention, 1-Isocyanato-2-(methoxymethyl)-3-methyl-benzene can be produced at high yields.

The invention claimed is:

1. A method for manufacturing an isocyanate compound represented by formula (2)

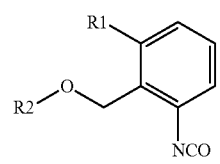

wherein R1 represents a methyl group, an ethyl group, a cyclopropyl group, a chlorine atom, a bromine atom, or a methoxy group; and R2 represents an alkyl group having 1 to 6 carbon atoms, comprising reacting an aniline compound represented by formula (1)

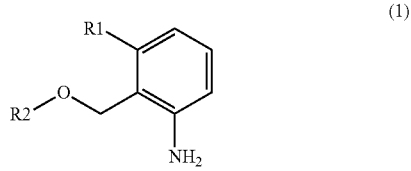

wherein R1 and R2 are defined as above
with a phosgene compound in at least one inert solvent at a temperature of from 40° C. to a boiling point of the inert solvent,
wherein the reaction is carried out in the absence of a tertiary amine.

2. The method according to claim 1, wherein
a) the aniline compound, and
b) the phosgene compound,
are added to a solution (S1) comprising the at least one inert solvent.

3. The method according to claim 2, wherein the addition of the aniline compound or of the phosgene compound occurs below the liquid surface of solution (S1).

4. The method according to claim 2, wherein the addition of the aniline compound and of the phosgene compound occurs below the liquid surface of solution (S1).

5. The method according to claim 3, wherein the addition is conducted via a dip pipe or a mixing nozzle.

6. The method according to claim 1, wherein R1 is methyl.

7. The method according to claim 1, wherein R2 is methyl.

8. The method according to claim 1, wherein R1 is methyl and R2 is methyl.

9. The method according to claim 1, wherein the temperature is from 50° C. to 100° C.

10. The method according to claim 1, wherein the temperature is from 60° C. to 95° C.

11. The method according to claim 1, wherein the at least one inert solvent is an aromatic solvent.

12. The method according to claim 1, wherein the at least one inert solvent is selected from the group consisting of benzene, alkylated benzenes, and halogenated benzenes.

13. The method according to claim 1, wherein the at least one solvent is toluene, xylene, chlorobenzene, or dichlorobenzene.

14. The method according to claim 1, wherein the at least one inert solvent is toluene.

15. The method according to claim 4, wherein the addition is conducted via a dip pipe or a mixing nozzle.

* * * * *